United States Patent [19]

Richardson

[11] 4,065,959

[45] Jan. 3, 1978

[54] PORTABLE VISCOMETER APPARATUS

[75] Inventor: Harold W. Richardson, Denver, Colo.

[73] Assignee: Richmore Company, Denver, Colo.

[21] Appl. No.: 748,632

[22] Filed: Dec. 8, 1976

[51] Int. Cl.$^2$ ............................................. G01N 11/06
[52] U.S. Cl. ........................................................ 73/56
[58] Field of Search ....................................... 73/55, 56

[56] References Cited

U.S. PATENT DOCUMENTS

| | | | |
|---|---|---|---|
| 2,564,892 | 8/1951 | Gerin | 73/56 |
| 2,743,605 | 5/1956 | Gamlen | 73/55 |
| 2,836,975 | 6/1958 | Euverard | 73/55 |
| 3,074,266 | 1/1963 | Sadler et al. | 73/55 |

Primary Examiner—Richard C. Queisser
Assistant Examiner—Joseph W. Roskos
Attorney, Agent, or Firm—Richard D. Law

[57] ABSTRACT

A portable viscometer, used in conjunction with a belt mounted computer, for making field viscosity measurements and for taking samples of various liquids such as paint mixes, asphalt cements, liquid asphalts, asphalt, emulsions, etc. A disposable cup, arranged at the bottom of a frame, permits the frame to be immersed in the fluid to be tested, a sample cup holder with fluid level probes is moved into position under the disposable cup and releasable stopper means permits fluid to drain from the disposable cup into the sample cup, with the computer timing the flow, and measuring the temperature.

6 Claims, 10 Drawing Figures

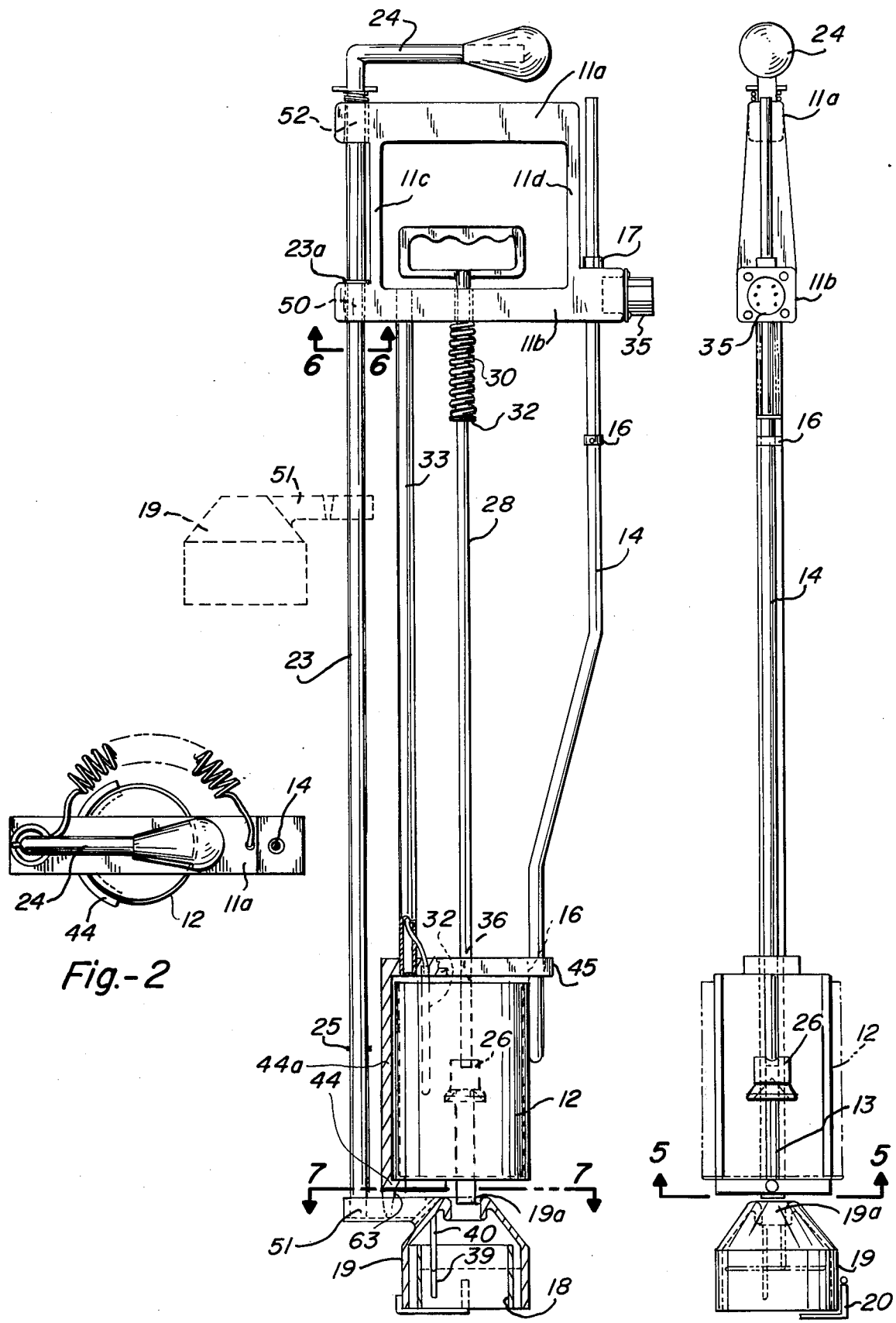

PORTABLE VISCOMETER APPARATUS

BACKGROUND AND PRIOR ART

The present invention relates to a portable viscometer which allows field viscosity measurements to be accurately taken of various liquids.

Viscosity, a property of fluid bodies resulting from molecular attraction which makes them offer resistance to flow, is an important indicia of the grade and quality of many liquid substances. For instance, in the road construction industry asphalt cements, liquid asphalts and emulsions are used in production of asphalt concrete for use in construction of roads and parking lots. The quality and grade of the asphalt cements, liquid asphalt or asphalt emulsions used determines in a large part the characteristics of the finished paved surface. Another reason being, during the refining process of asphalt products samples must be taken periodically and tested in the laboratory. This invention may be used as an intermediate quality control step. For this reason during road construction, it has become more prevalent to determine some of the characteristics of the asphalt cements, etc. used. Viscosity measurement is an accurate determinant, but it is mostly made in a laboratory using samples obtained in the field. This viscosity data can then be correlated to important characteristics of the finished paved surface, such as compression strength and resistance to deformation under stress and heat. Samples are usually taken from each truck or tank car load of asphalt used, and are therefore representative of the road section fabricated with that particular truck or tank car load.

In the paint industry viscosity is, also, an important indicia of the quality and grade of the paint. Laboratory viscosity tests are often performed on paint samples, but it would be advantageous to have "in the plant" viscosity measurements.

In one type of test, the viscosity of a liquid, at a certain temperature, can be determined by timing the flow of a known amount of the liquid under a standard head through a standard orifice. In the past, however, accurate viscosity measurement of this type had to be made in laboratories because there was no means for accurately performing the tests in the field. This procedure can cause difficulties because the laboratory tests often cannot be performed until long after the road section is completeed or long after the paint has been mixed and packaged for sale.

PRIOR ART

A continuous viscometer is shown in U.S. Pat. No. 3,290,923 to Norcross, which uses a cyclic sampling. The Kleiss U.S. Pat. No. 3,512,394 incorporates a temperature-time relation to a complicated laboratory viscometer. A laboratory viscometer 13, shown in U.S. Pat. No. 2,668,441 to Peterson, particularly is directed to the stopper arrangement for release of fluid during a viscometer testing.

BRIEF DESCRIPTION OF THE INVENTION

Utilizing the present invention, instantaneuos field viscosity measurements can be made, allowing construction and manufacturing processes to be controlled in the field during the operation itself. Also, with this invention, after the field viscosity measurements have been made, a representative sample may be retained which can then be transported to the laboratory for further tests.

The apparatus of this invention comprises, basically, a portable elongated frame means which supports an open top disposable cup, a movable sample cup support means mounted for movement in the frame means and for positioning a sample cup under the paper cup, and valving and draining means integral with the frame means for draining the sample fluid from the paper cup through a sized orifice to the sample cup. Temperature and timing sensors mounted on the frame are read out on an operator's belt mounted computer for measuring the temperature and timing the flow of a known amount of liquid.

For taking a viscosity measurement, the frame means is first lowered by the operator into a tank of liquid to fill the disposable paper cup. A sample cup is positioned under the paper cup, and liquid is allowed to flow from the disposable paper cup through the drain means. Sensors measure the temperature of the liquid and the time it takes for a known quantity of liquid to flow into the sample cup. This data is read out on the computer and can be used to determine the viscosity of the liquid.

OBJECTS OF THE INVENTION

It is, therefore, among the objects and advantages of the present invention to provide a method and apparatus for making accurate field viscosity measurements of fluids such as asphalt cement, liquid asphalts, asphalt emulsions, paint mixes, etc.

Another object of the invention is to provide a portable viscometer, with a disposable container for making field viscosity measurements, and provides a storable sample of fluid.

Another object of the invention is to provide an apparatus for obtaining field viscosity measurements and laboratory samples of such fluids as paint mixes, asphalt cements, liquid asphalts, asphalt emulsions, etc.

These and other objects and advantages of the invention may be readily ascertained by referring to the following description and appended illustrations.

BRIEF DESCRIPTION OF THE DRAWINGS

FIG. 1 is a side elevational view, in partial cross section of a portable viscometer, according to the invention.

FIG. 2 is a top view of the device of FIG. 1, without a disposable cup.

FIG. 3 is a front elevation view of the device of FIG. 1.

DESCRIPTION OF THE PREFERRED EMBODIMENT

Figure 4:
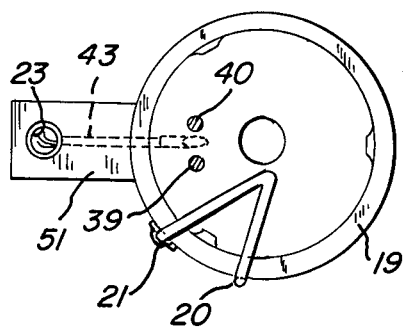
FIG. 4 is a detail of the movable sample cup support according to the invention.
Figure 7:
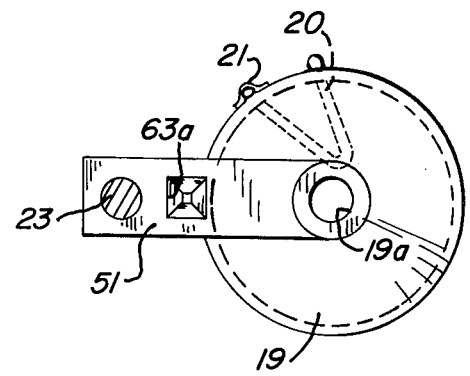
FIG. 7 is a cross-sectional view of the movable sample cup support.
Figure 6:
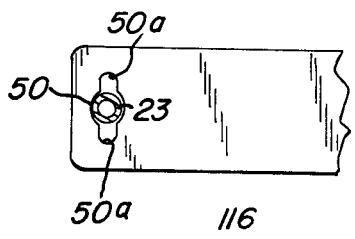
FIG. 6 is an enlarged detail of means for locking a sample cup support means.

Referring now to FIG. 1, the frame means of the apparatus, generally denoted as 10, has manipulating handle 11 including a member 11a which can be grasped by the operator for transporting and submerging the frame in a tank of liquid such as asphalt. The frame includes a main vertical support 33, secured to its lower member 11b, and a bottom frame bar 45, from which depends a cup mount 44. The upper member 11a is held apart from lower member 11b by uprights 11c and 11d.

A disposable round cup 12 is inserted into the cup mount 44 of the frame 10. The cup may be made of any disposable material which can withstand the temperature extremes of hot test liquids. In this embodiment of the invention, the cup 12 is made of a cardboard or heavy paper, open at the top and has a pressed on metal bottom closure 27. Axially aligned and depending upwardly from the cup bottom 27 is a pipe 13, with a sized opening. This upstanding orifice pipe may be integrally attached, or in some instances only a hole provided, explained below.

Figure 5:
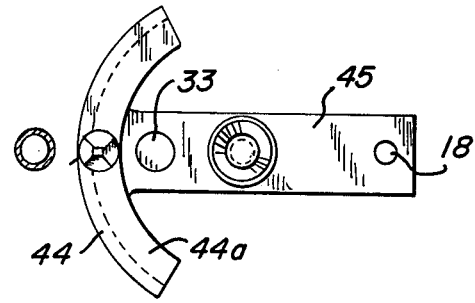
FIG. 5 is a cross-sectional view of the frame of FIG. 3 taken along section lines 5—5.
Figure 8:
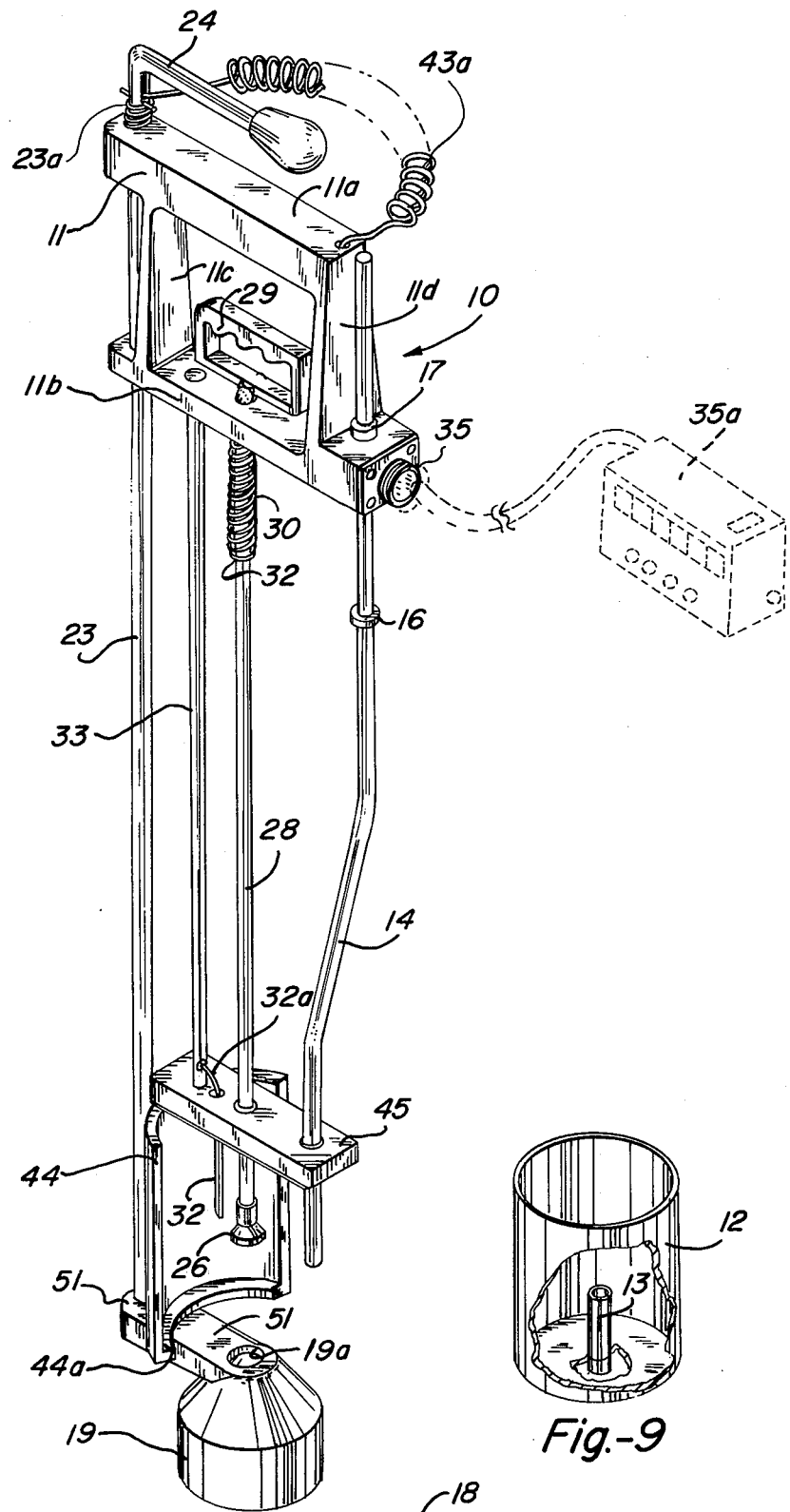
FIG. 8 is perspective view of one form of the invention.
Figure 9:
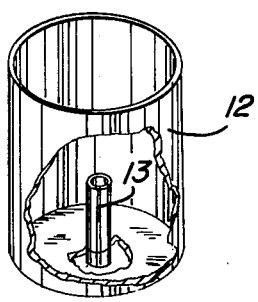
FIG. 9 is a cut-away perspective of one form of a disposable cup.
Figure 10:
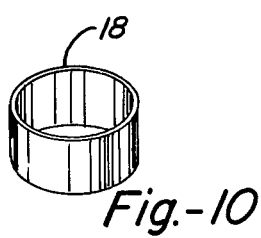
FIG. 10 is a perspective of one form of a sample cup.

The cup support 44 in the frame 10 includes a curved plate 44, which has a radial lip 44a, on which a cup rests. As shown in FIG. 5, plate 44 is curved to mate with the curved surface of the round cup 12. Vertical movement of the paper cup 12 is prevented by plate 45. A vertically movable cup retaining rod 14 retains the paper cup in the frame 10. The rod is slidably mounted in bores 15 and 16 within the frame handle 11 and plate 45. This rod 14 can be pulled up by the operator for inserting and removing the paper cup 12 and pushed down for retaining the paper cup after it has been inserted. The movement of the rod is limited by a lower step on the rod 14, and stop 17, and an upper shaft collar 16.

With the cup retainer moved to the upper position, the paper cup may be easily inserted into the frame 10 and retained for support. This maintains the temperature probe 32 in the cup in position to contact the sample fluid.

A sized sample cup 18, which may be made of tin, or other materials, is placed into movable support means 19 and it is held in support 19 by a wire spring 20 (FIG. 4) pivoted in a base 21. Alternately, a spring clip or other latch attached to the sample cup supports 19 may be used in place of the spring 20 to hold the sample cup 18.

The sample cup support 19 is mounted on a slidable tubular support 23 with handle means 24 attached to its top for manipulation of the sample cup support. This support 23 is slidably mounted in two bores 50 and 52 within the frame handle 11.

The sample cup support 19 is mounted on a bar 51 which in turn is supported on tubular member 23. The handle 24 permits easy rotation of the tubular member 23, which rotates the cup support 19 directly under the frame or 180° out from that position. In the latter position, the cup support can be elevated by pulling up on the handle, so as to locate the cup support a substantial distance above the paper cup holder 44, attached to main tubular frame support 33. A pin 23a extended through the support 23 is arranged to mate with slots 50a on opposed sides of the opening 50 and similar slots in opening 52. This permits aligning the pins with the slots to permit the tubular member 23 to slide up and down. Also, by turning the pin 90° to the slots, the support is held in a position. An opening 19a in the top of the sample cup holder permits liquid to flow from the upper cup into the sample cup when the outlet of the cup is opened.

A paper (or other material) open top cup or container includes, in one form, an upstanding outlet tube 13. This tube is arranged to be closed or opened by a valve 26 mounted on the end of reciprocable rod 28. The rod 28 is controlled by a handle 29 in the frame handle 11. The rod 28 is biased in the down position by a tension spring 30 bearing against a spring stop 32.

The sample cup support means 19 may be rotated and raised from the position under the paper sample cup, shown in FIG. 1, to the phantomed position. To obtain the phantomed position, the operator depresses handle 24 until the bore 63a on the bar 51 holding the sample cup support 19 clears the centering pin 63, which centers the support in alignment with the disposable cup. The handle may then be rotated 180° and the sample cup support raised to the phantom position.

Once the sample cup support is in the upper phantom position the handle 24 is again rotated so that a pin 25 in a lower portion of the tube 23 is out of position with respect to the slots in bore 50, to keep the assembly from dropping.

The disposable open-top-cup holder 44 includes the curved portion 44, against which the cup bears, and a ledge or inwardly directed flange 44a. A cup seats on the flange 44a and is held against the member 44 and on the ledge by the holder 14. For inserting the cup, the holder 14 is raised, and is lowered for holding the cup in position. The distance between the flange 44a and the upper bar 18 is sufficient to accommodate a cup without undue movement and permit it to be held in the frame.

The disposable cup 12 may be formed of paper, plastic, light metal or the like. In one form, it may be made of relatively stiff paper (rolled with adhesive to form a tube) with a rolled-on end made of metal or other relatively rigid material. A liquid release tube may be secured in the bottom end to contact the valve 26, for closing the tube. The valve 26 may also be pulled up from the tube to open the same. In another form, the rod 28 may be made long enough to contact the bottom of an inserted cup. In this modification the cup will have a central aperture which is closable by the valve 26, and openable by pulling the handle 29. Where desired, the tube 13 may extend a short through the bottom for directing the liquid in the sample cup 18.

The sample cup 18 may be disposable, if desired, or may be a storage cup for a sample. In the latter case, the cup could be fitted with a cap for transport of the sample to a laboratory. This provides for collecting and storing samples as desired. Of course, the samples may be numbered or otherwise identified to provide correlation with the viscosity measurement made with the present instrument in the field.

The sample cup holder 19 includes level probes 39 and 40 which depend downwardly from the inside top of the holder 19. These extend into a cup placed in the holder and are arranged to sense the level of the liquid flowing into the cup. The leads 43 from the level sensors extend through the bar 51 and through the tube 23. The leads exit the top of tube 23 to a retrieving coil lead 43a which enters the front part of the handle 11a. The lead extends through a bore in the handle to a connector 35. The connector 35 is arranged to be connected to the mating part of the connector having leads to belt supported time-temperature indicator 35a on computer having a visible (or other) read-out. The coiled lead permits the tube 23 to be raised while retaining the connection between the level sensors and the connector 35. A temperature sensor 32 is provided with its leads 32a extending up through the tube or hollow rod 33 to the handle bottom 11b. These leads pass through a bore in the handle and connect to connector 35.

For use, the disposable cup 12 is inserted into the frame by lifting the holder 14. The cup telescopes over the valve and temperature sensor and seats on the ledge 44a. The holder 14 is pressed downwardly to hold the cup against the curved member 44 on the ledge 44a. The sample cup 18 is telescoped into the holder 19 and secured in position by the holder 20. The handle 24 is rotated to permit the cup holder to be pulled into the upper position.

The end of the unit may then be immersed in the liquid to be tested to a depth to permit the liquid to flow over the open top of the disposable cup, to fill the same.

After the frame 10 has been withdrawn from the tank, the movable support 19 with an enclosed sample cup 18 is rotated into the position under the paper cup 12, shown in FIG. 1. The cup holder is rotated to a position where the centering pin will enter the bore 51. A spring 23a biases the tube 23 upwardly to hold the cup holder in place on the centering pin. The operator then pulls handle 29 to open the tube 13 by lifting the stopper valve 26. The liquid begins to flow through tube 13 into the tin sample cup 18. The tube 13 is located with respect to the paper cup 12 and the tin sample cup 18 such that all of the flowing liquid exits into the tin sample cup. The opening of tube 13 is of a predetermined size for the material, sizing depending on the nature of the liquid being tested. The flow of liquid from the paper cup 12 through the orifice of pipe 13 to the tin sample cup 18 is timed by the two sensors 39 and 40.

Sensor 39 is placed towards the bottom of tin sample cup 18 and sensor 40 is placed towards the top. The distance between the pins defines a known volume. When the liquid reaches the lower sensor 39 in the tin sample cup 18, a timer is activated in the computer, when the liquid reaches the level of sensor 40 the timer is shut off and the elapsed time is noted on the computer read-out. Thus, the time it takes for a known quantity of liquid to flow through the orifice of pipe 13 under the head of liquid contained in paper cup 12, may be determined, and this data along with the temperature data also indicated by the read-out, allows the viscosity of the liquid to be calculated.

The sample cup 18 is then removed from the holder 19. A lid (not shown) can be affixed to this cup 18 and the cup may be transported to the laboratory for further tests of the liquid.

The paper cup 12 can then be removed from the frame 10 by lifting holder 14. This paper cup 12 may be disposed of, when desired, the sized pipe 13 may be reclaimed and be inserted in a clean paper cup. The frame 10 may then be cleaned by any suitable method, such as immersing it in a container having a suitable solvent, and a clean tin sample cup 18 and paper cup 12 may be inserted in the frame 10 for the next sampling.

A suitable material may be used in fabricating this apparatus. The invention has found that aluminum works well because of its non-sparking characteristics and heat conductivity, which may be an important consideration in some environments.

The foregoing apparatus has been described fully so as to enable a clear understanding of the present invention and to allow its practice. However, it may be that those skilled in the art will foresee changes and modifications in the foregoing description of the present invention without departing from the scope of the invention. Therefore, it is intended by the appended claims to cover all such changes and modifications as fall within the true spirit and scope of the present invention.

What is claimed is:

1. A field or portable viscometer, comprising:
   a. portable elongated frame means;
   b. support means at one end of said frame means for releasably supporting an open top disposable cup for receiving a fluid for sampling, the disposable cup having a single small opening the bottom thereof;
   c. releasable support means on said frame means for holding a sample cup and for positioning the sample cup beneath the disposable cup for receiving fluid draining from the disposable cup;
   d. drain means, including a predetermined sized openings, for draining the fluid from the disposable cup to the sample cup;
   e. valve means for opening and closing said drain means; and
   f. means for measuring the temperature of the fluid and for timing the flow of a known amount of the fluid through the sized opening.

2. A portable viscometer as recited in claim 1 wherein the means for measuring the temperature of the fluid and for timing the flow of a known amount of the fluid through the sized opening comprises:
   a. temperature sensor means mounted to contact the contents of the disposable cup;
   b. a first time start sensor and a second time stop sensor connected to a belt mounted computer, said sensors being mounted in position to contact the contents of the sample cup, and said sensors being arranged to conjointly define a known volume by a staggered location, such that when the level of fluid draining into the sample cup reaches the first sensor, a timer is activated and when the level reaches the second sensor the timer is deactivated.

3. A portable viscometer as recited in claim 1 wherein the drain means comprises:
   a drain tube with a sized opening affixed to the hole in the disposable cup and connecting the disposable cup through said frame means to the sample cup.

4. A portable viscometer as recited in claim 1 wherein the valve means comprises:
   a. a stopper arranged to open and close the opening of said drain tube;
   b. said stopper connected to a rod, slidably mounted in said frame means, with a spring for holding said stopper against said drain tube and a handle for manual actuation.

5. A portable viscometer as recited in claim 1 wherein the frame means comprises:
   a. a handle;
   b. two plates connected by tubing to said handle, one of said plates with a lip for supporting the disposable cup, the other of said plates for preventing vertical movement of the disposable cup;
   c. a slidable rod mounted in bores in said handle and said plates, for retaining the disposable cup on said plates;
   d. a plug mounted in said handle for attaching a belt mounted computer to sensors placed in the disposable cup and the sample cup;
   e. a centering pin mounted on one of said plates, for aligning said movable sample cup support means and the sample cup, under the disposable cup.

6. A portable viscometer as recited in claim 5 wherein the movable support means for holding the sample cup comprises:
   a. a cup holder with an opening at the bottom for inserting the sample cup and a plurality of smaller openings at the top for draining the fluid into the sample cup, and for introducing sensors into the sample cup;
   b. a leaf spring attached to the cup holder, with a tab for holding the sample cup in the cup holder;
   c. a tube with a handle, attached to said cup holder, for mounting said cup holder in bores in said frame means and for rotating and moving said cup holder with respect to said frame means; and
   d. a spring between said tube and said frame means for holding said cup holder against said frame means.